United States Patent [19]

Sasaki

[11] 4,102,649

[45] Jul. 25, 1978

[54] METHOD AND DEVICE FOR AGITATING A LIQUID

[75] Inventor: Toshio Sasaki, Tokyo, Japan

[73] Assignee: Fujizoki Pharmaceutical Co., Ltd., Tokyo, Japan

[21] Appl. No.: 798,333

[22] Filed: May 19, 1977

[30] Foreign Application Priority Data

May 25, 1976 [JP] Japan ................................ 51-60282

[51] Int. Cl.[2] ...................... G01N 1/18; G01N 33/16; B01F 11/00

[52] U.S. Cl. ...................................... 23/259; 366/114; 23/292

[58] Field of Search ..................... 23/259, 292, 253 R, 23/230 R; 259/83, 56; 366/114

[56] References Cited

U.S. PATENT DOCUMENTS

| | | | |
|---|---|---|---|
| 3,488,156 | 1/1970 | Good et al. | 23/253 R |
| 3,876,379 | 4/1975 | Ghim | 23/230 R |

*Primary Examiner*—R.E. Serwin

*Attorney, Agent, or Firm*—Burgess, Ryan and Wayne

[57] ABSTRACT

A liquid contained in a hole formed in a tray is agitated by horizontally vibrating the tray, said tray being connected to a vibration plate and the vibration plate being caused to vibrate by means of an electromagnet or an eccentric wheel.

1 Claim, 6 Drawing Figures

METHOD AND DEVICE FOR AGITATING A LIQUID

BACKGROUND OF THE INVENTION

The present invention relates to a method and a device for agitating a liquid mixture, and is particularly useful for agitating a mixture of a serum with a dilutant.

One type of serial dilution machine is shown in U.S. Pat. No. 3,536,449, the disclosure of which is incorporated herein by reference. The principle of the method disclosed in said patent is illustrated in FIG. 1(*a*), FIG. 1(*b*) and FIG. 1(*c*) of the accompanying drawings. FIG. 1(*a*) is a plan view of a tray of the serial dilution machine. The tray 1 contains a plurality of rows of holes 2. The holes each have an inside diameter of about 6mm and a depth of about 10mm. FIG. 1(*b*) is a sectional view of a dilution rod (a rod for use in diluting). The dilution rod 5 has a hemispherical bowl 4 at an end of the rod. The bowl 4 has a diameter of about 3mm. FIG. 1(*c*) is a sectional view of the tray. A predetermined quantity of dilutant liquid 3 (a liquid for use in dilution of a serum) is contained in the holes 2 of the tray 1. The tray 1 is made of, for example, plastic, and the dilution rod is made of, for example, stainless steel. The size of the tray depends on the number of the holes.

Serial dilution is performed by using such a serial dilution machine as follows:

The dilution rod 5 is dipped in a serum to be diluted. A fixed quantity of the serum is retained in the bowl 4. The bowl 4 containing the serum is dipped in the hole 2 containing a dilutant liquid 3, and then the dilution rod is rotated to mix and dilute the serum with the dilutant liquid 3. The dilution rod having the diluted serum contained in the bowl is inserted in the next hole containing a dilutant liquid and then rotated as described above. By repeating such a procedure several times, serums diluted with a dilutant liquid can be obtained in each of the holes. In this case, if a quantity of a liquid contained in the bowl is equal to a quantity of a liquid contained in the hole, the serum will be diluted two, four, eight . . . times in turn.

In the conventional serum dilution machine, when many kinds of serums will simultaneously be diluted, many dilution rods must simultaneously be rotated as shown in U.S. Pat. No. 3,536,449. In such a machine, complex mechanisms and structures are required, and further, agitation of a liquid in the holes cannot be effected without the dilution rod.

Accordingly, an object of the present invention is to provide complete agitation of a liquid without the dilution rod, and complete mixing or diluting without rotation of the dilution rod.

IN THE DRAWING:

FIG. 1(*b*) is a sectional view of a dilution rod;

FIG. 1(*c*) is a sectional view of the tray of FIG. 1(*a*);

FIG. 2(*b*) is a plan view of a tray incorporating agitation means according to an alternative embodiment of the invention; and FIG. 2(*c*) is a sectional view of the tray shown in FIGS. 2(*a*) and 2(*b*).

As herein described, in a device for agitating (mixing and diluting) a liquid according to the present invention, the tray containing liquid retention holes is caused to vibrate instead of agitating the liquid by rotating a dilution rod, as described in U.S. Pat. No. 3,536,449.

Figure 1A:
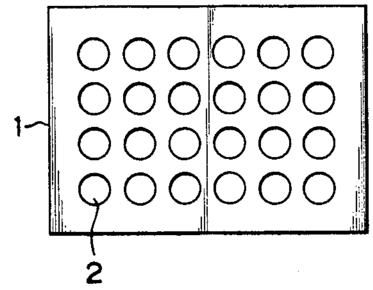
FIG. 1(*a*) is a plan view of a tray used in a serial dilution machine.
Figure 1B:
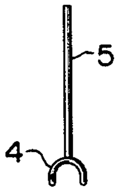
Figure 1C:
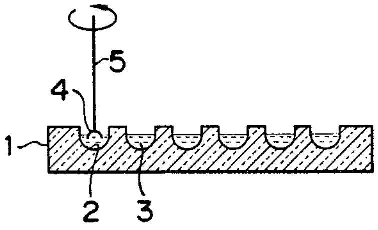
FIG. 1c PRIOR ART
Figure 2A:
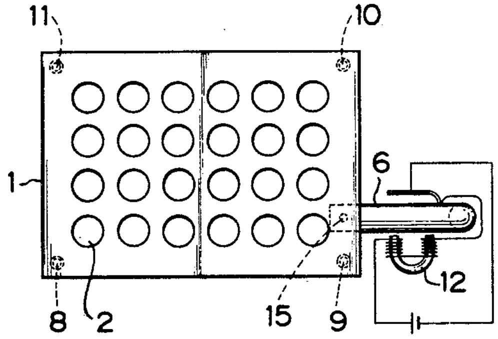
FIG. 2(*a*) is a plan view of a tray incorporating agitation means according to a preferred embodiment of the present invention.
Figure 2C:
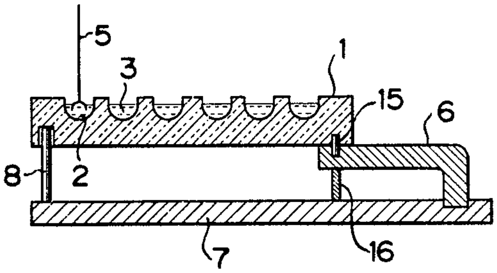

Complete agitation (mixing and diluting) of a liquid in the hole cannot be achieved by causing the tray only to vibrate horizontally in simple manner. The present invention is illustrated in FIG. 2 of the accompanying drawings.

Figure 2B:
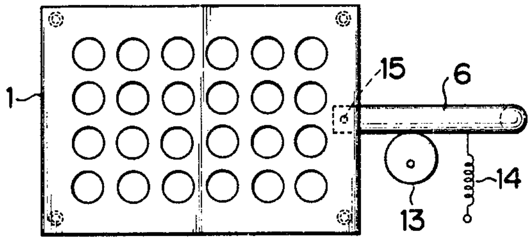

One end of a vibration plate or rod 6 made of a metal or a nonmetal is pivotably connected to the tray 1 by a pivot pin 15 in an optional position thereof, and the opposite end of the vibration plate 6 is rotatably attached to the base plate 7. The props 8, 9, 10 and 11 are fixed to the base plate 7, and the tray 1 is supported by the props 8, 9, 10 and 11. The tray is not fixed to the props, and is slidably movable thereon, so as to be able to vibrate. The vibration plate 6 is caused to vibrate by an electromagnet 12 (FIG. 2*a*) or an eccentric wheel 13 (FIG. 2*b*). The vibration of the vibration plate 6 is coupled to the tray 1, and the tray 1 is caused to vibrate horizontally in a nonlinear manner, because the end of the vibration plate 6 vibrates in a circular arc. The eccentric wheel 13 may be rotated by means of a motor (not shown), and the vibration plate 6 is urged against the wheel 13 by a spring 14.

As illustrated above, a liquid 3 contained in the hole 2 can easily be agitated by the vibration of the tray as shown above even without using the dilution rod. Therefore, the dilution rod carrying a serum to be diluted is inserted in the first hole containing a dilutant liquid and then the rod is inserted in the next hole in turn, the diluted serums being mixed in the holes by the vibration of the tray and without rotation of the dilution rod.

In the device as shown above, when the vibration is effected by an electromagnet, the vibration plate is made of iron or another magnetic material, and when the vibration is effected by an eccentric wheel, the vibration plate may be made of aluminum or plastic.

The tray may be supported by three or five props instead of four props. The ends of the vibration plate 6 may be connected at an optional position of the tray 1 and the base plate 7, respectively. One end of the vibration plate 6 may be attached to one of the props 8, 9, 10 and 11 supporting the tray 1, instead of the base plate 7.

The tray 1 may be mounted on a plate (not shown) which is connected to the vibration plate 6, instead of directly connecting the tray 1 to the vibration plate 6. In this way, the tray can be removed from the device to replace the tray by another tray, since the tray needs to be often exchanged for washing.

The device of the present invention can be used for agitating or mixing a liquid contained in a hole formed in a tray, and further may be used for diluting a serum by employing a dilution rod as already described above.

When the tray is vibrated by an electromagnet 12, vibrational movement of the rod 6 is facilitated by a resilient metal strip 16 extending vertically from the part of the rod 6 adjacent the pivot pin 15 to the base plate 7.

What is claimed is:

1. In a serial dilution machine, the combination comprising:

a tray having a plurality of liquid receiving holes formed therein;

a horizontal support plate having a plurality of vertical props extending therefrom, said tray being slidably supported on said props;

a vertical pivot pin in an optional poition of said tray;

an L-shaped vibration rod having one end mounted to said pivot pin to rotationally couple said member to said tray;

said rod having another end pivotally mounted to said support plate for rotation about a vertical axis;

means for causing nonlinear rotational vibration of said member in a circular arc in only a horizontal plane with respect to said support plate to vibrate said tray via said pivot pin to thereby agitate any liquid within said holes; and spring means coupled between a point of said rod adjacent said pivot pin and said support plate.

* * * * *